United States Patent [19]

Murphy et al.

[11] Patent Number: 5,417,963
[45] Date of Patent: May 23, 1995

[54] HYDROPHILIC POLYMER-COATED MICROCRYSTALLITES OF BICARBONATE INGREDIENT

[75] Inventors: Richard T. Murphy, Belle Mead; M. Stephen Lajoie, Basking Rdige, both of N.J.

[73] Assignee: Church & Dwight Co., Inc., Princeton, N.J.

[21] Appl. No.: 219,873

[22] Filed: Mar. 30, 1994

Related U.S. Application Data

[63] Continuation of Ser. No. 53,834, Apr. 27, 1993, abandoned, which is a continuation-in-part of Ser. No. 986,916, Dec. 8, 1992, Pat. No. 5,354,553.

[51] Int. Cl.[6] .......................... A61K 7/32; A61K 7/34
[52] U.S. Cl. ........................................ 424/65; 424/66; 424/67; 424/DIG. 5; 514/965
[58] Field of Search ................... 514/965; 424/65, 66, 424/67

[56] References Cited

U.S. PATENT DOCUMENTS

| | | | |
|---|---|---|---|
| 4,382,079 | 5/1983 | Marschner | 424/65 |
| 4,822,602 | 4/1989 | Sabatelli | 424/65 |
| 4,832,945 | 5/1989 | Osipow et al. | 424/65 |
| 4,992,326 | 2/1991 | Dabi | 428/283 |
| 5,230,958 | 7/1993 | Dabi | 424/489 |

Primary Examiner—José G. Dees
Assistant Examiner—Dwayne C. Jones
Attorney, Agent, or Firm—Charles B. Barris

[57] ABSTRACT

This invention provides a powder composition which is composed of particles consisting of a hydrophilic polymer coating having an encapsulated core matrix content of at least two microcrystallites of water-soluble inorganic compound such as sodium bicarbonate. In one embodiment a present invention powder composition has a content of hydrophilic polymer-coated bicarbonate microcrystallites, and a cosmetically safe anti-caking agent such as talc, and has utility as a baby powder product.

13 Claims, 1 Drawing Sheet

HYDROPHILIC POLYMER-COATED MICROCRYSTALLITES OF BICARBONATE INGREDIENT

CROSS-REFERENCE TO RELATED PATENT APPLICATION

This application is a continuation of application Ser. No. 08/053,834, filed Apr. 27, 1993, now abandoned, which is a continuation-in-part of Ser. No. 07/986,916, filed Dec. 8, 1992, now U.S. Pat. No. 5,354,553.

BACKGROUND OF THE INVENTION

Anhydrous antiperspirant stick systems have good consumer acceptance primarily due to the ease of application to the skin, good cosmetic esthetics and an acceptable degree of effectiveness. Previous to the development of anhydrous stick systems, numerous water-based systems were developed in which the active astringent salts were solubilized in a thickened or gelled composition. This is exemplified in U.S. Pat. Nos. 2,732,327; 2,857,315; 3,255,082; and 3,928,557. The water based systems are difficult to apply to the skin, and their consistency and effectiveness are variable.

Many anhydrous stick compositions have been described in the literature which attempt to improve the delivery and the effectiveness of their antiperspirant and deodorant characteristics. Antiperspirant stick systems consisting of low molecular weight monohydric alcohols in conjunction with polyhydric alcohols are described in U.S. Pat. No. 4,137,306. These sticks have the advantage of quicker drying rates, but the residue of the polyhydric alcohols in combination with the astringent salts produces a high degree of tack, and their effectiveness is limited to the type and amount of astringent salts that could be incorporated in the stick matrix.

Anhydrous stick compositions that suspend the aluminum salt in a hydrophobic matrix are described in U.S. Pat. No. 4,049,792. These compositions employ waxy materials and long chain fatty esters to form a stick that delivers the active astringent salts to the skin.

Cosmetic stick compositions made in accordance with these embodiments are greasy, and the active astringent salt is enveloped in a manner that prevents maximum performance. To alleviate this inherent negative characteristic, volatile silicone fluids replacement of the less volatile long chain fatty esters is described in U.S. Pat. No. 4,126,679. This disclosure teaches the advantage of utilizing a volatile non-staining liquid such as cyclic dimethylpolysiloxanes (referred to as volatile silicones), in combination with various types of waxes, as a carrier for the active astringent salts in an antiperspirant stick composition. Similar antiperspirant stick compositions containing volatile silicones are described in U.S. Pat. Nos. 4,511,554; 4,980,156; and 4,985,238.

With respect to deodorant activity, sodium bicarbonate has long been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602 and U.S. Pat. No. 4,832,945.

However, the development of a practical and effective antiperspirant composition in cosmetic stick or roll-on form which is also capable of deodorization, and which qualifies for consumer acceptability, presents many factors which are unique. Because alkali metal and ammonium bicarbonate have only limited solubility in water, alcohol and other solvents, the preparation of a composition suitable for dispensing in cosmetic stick or roll-on form has involved many processing obstacles. In addition to the problem of limited solubility, a bicarbonate ingredient is incompatible with the active astringent salts and with other ingredients of conventional stick compositions. Also, the dimensional stability of the cosmetic product containing bicarbonate ingredient, and the esthetic appearance and the "feel" on the skin, are just a few of the additional difficulties encountered in the preparation of a low residue antiperspirant-deodorant cosmetic product.

Another problem associated with the incorporation of a bicarbonate deodorant ingredient in an antiperspirant formulation is the tendency for the high density bicarbonate salt particles to settle in the fluid medium during processing. Also, under the elevated temperature conditions required for the admixing and blending of ingredients, bicarbonate degradation and evolution of carbon dioxide and water occur.

OBJECT OF THE INVENTION

There is continuing interest in the development of bicarbonate-containing cosmetic products which exhibit deodorizing activity, and in improved forms of bicarbonate deodorant ingredients.

Accordingly, it is an object of this invention to provide cosmetic products which contain a novel form of bicarbonate deodorant ingredient.

It is another object of this invention to provide a powder composition composed of particles of hydrophilic polymer-coated bicarbonate microcrystallites.

Other objects and advantages of the present invention shall become apparent from the accompanying description and examples.

DESCRIPTION OF THE INVENTION

Figure 1:
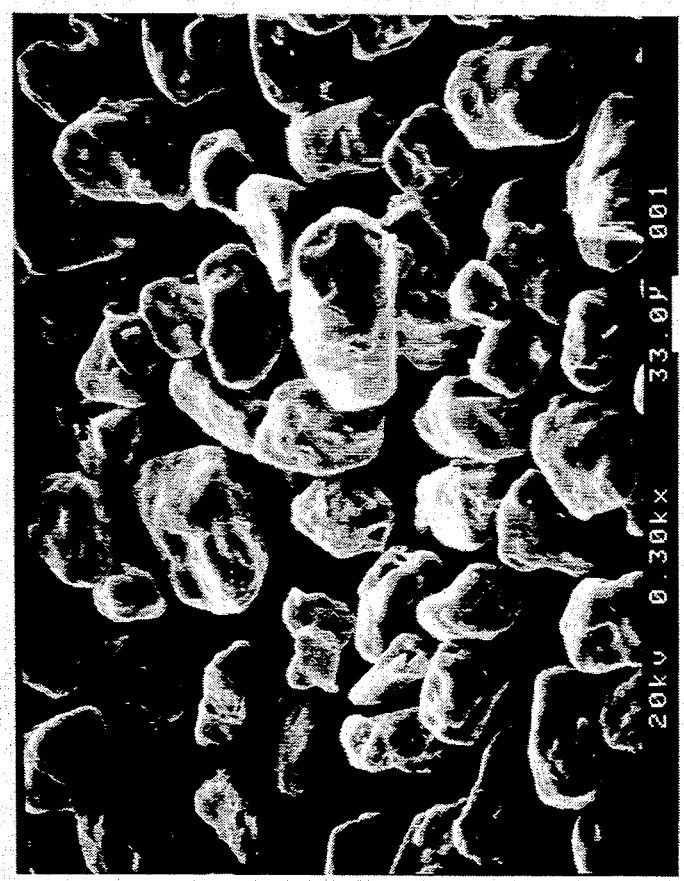
FIG. 1 is a scanning electron microscope photomicrograph illustrating particles of starch-coated sodium bicarbonate deodorant.

One or more objects of the present invention are accomplished by the provision of a powder composition which is composed of particles having an average particle size between about 5–60 microns, and an average dimensional axial ratio between about 1–2.5 to 1, and wherein the particles comprise a hydrophilic polymer surface coating having an encapsulated core matrix content of at least two crystallites of water-soluble inorganic compound selected from alkali metal bicarbonate and ammonium bicarbonate.

The term "particle size" as employed herein refers to the largest size dimension of a particle.

The term "dimensional axial ratio" as employed herein refers to the ratio of the largest axial diameter to the other axial diameters.

The term "water-soluble" as employed herein refers to a bicarbonate salt which has a solubility of at least about five grams per 100 grams of water at 25° C.

The terms "crystallite" and "microcrystallite" as employed herein refer to micro-size crystalline particles of bicarbonate salt.

The encapsulated microcrystalline bicarbonate ingredient of an invention powder composition is selected from alkali metal and ammonium bicarbonates, such as sodium bicarbonate, potassium bicarbonate and ammonium bicarbonate, and mixtures thereof. The encapsulated bicarbonate core matrix can contain up to about 30 weight percent, based on the weight of bicarbonate ingredient, of an alkali metal or ammonium carbonate compound in admixture with the bicarbonate crystallites.

The encapsulated bicarbonate crystallites in the core matrix have an average particle size between about 0.5–30 microns. In a typical embodiment the encapsulated bicarbonate crystallites have a particle size distribution in which at least 80 percent of the particles have a particle size in the range between about 0.1–5 microns.

FIG. 1 is a Scanning Electron Microscope photomicrograph illustrating particles of starch-coated sodium bicarbonate deodorant. The particle size distribution substantially is in the range between about 10–40 microns, and each particle contains an average of about 2–10 bicarbonate crystallites in the core matrix.

The bicarbonate crystallites are "sandlike" and approximately spherical in configuration. Bicarbonate crystallites which are spheroidal in shape can be obtained by subjecting particulate bicarbonate to an air-jet pulverizing treatment, in which two air-jets containing entrained bicarbonate particles are impinged at high velocity. The resultant pulverized bicarbonate is recycled until the desired crystallite size distribution is obtained. The pulverized bicarbonate product can be sized into fractions as suitable for end-use purposes.

The presence of at least two crystallites of bicarbonate salt in each hydrophilic polymer-coated core matrix is attributable to the micro-size of the crystallites. Some of the microcrystallites aggregate to form crystallite agglomerates containing between about 2–10 primary crystallites. Coating of the agglomerates yield particles which contain between about 2–10 bicarbonate crystallites in the core matrix of hydrophilic polymer-coated particles.

Similar coated particles are obtained when during a coating procedure with a hydrophilic polymer solution two or more single bicarbonate crystallites, with a liquid surface coating of hydrophilic polymer solution, make contact and coelesce into coated particles containing two or more bicarbonate crystallites in the core matrix.

The application of the hydrophilic polymer coating to the core matrix particles is accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethylformamide, and the like, as appropriate for a selected polymer species. A coating polymer also can be applied in the form of an emulsion or suspension. After the coating medium is applied to the particles, the solvent medium is removed by evaporation, thereby forming a Continuous film coating which encapsulates the bicarbonate crystallites as demonstrated in Example I.

Another method of invention powder composition preparation is by slow addition of an aqueous solution of bicarbonate salt to a water-miscible organic solvent solution of a hydrophilic polymer, to form a suspension of precipitated bicarbonate microcrystallites in the organic solvent medium. Removal of the solvent medium yields hydrophilic polymer-coated bicarbonate microcrystallites as demonstrated in Example III.

As an alternative procedure the solvent component of the suspension admixture is partially removed, and the remaining concentrated suspension admixture is blended as a deodorant ingredient with organic ingredients in the formulation of a cosmetic stick or roll-on personal care product. The blending of the diverse miscibility phases serves to disperse the deodorant ingredient in the form of hydrophilic polymer-coated bicarbonate microcrystallites in accordance with the present invention.

The coating thickness on the particle surfaces typically will vary in the range between about 0.1–20 microns. The coating can consist of a single layer or multiple layers. The polymeric coating can constitute between about 5–50 weight percent of the total dry weight of the coated particles.

The hydrophilic polymer employed for coating the ingredient particles is selected from water-soluble and water-dispersible organic polymers. A mixture of polymers can be employed, and a content of between about 0.5–40 weight percent of a water-insoluble polymer, based on the coating weight, can be included.

The term "hydrophilic" as employed herein refers to an organic polymer which has a water-solubility of at least about one gram per 100 grams of water at 25° C.

Suitable hydrophilic polymers for coating particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, polyacrylamide, and the like. Polyvinyl acetate is illustrative of a water-insoluble polymer which can be included as an additional coating component to moderate the hydrophilicity of the coating.

The rate of particle matrix bicarbonate release from the particle core under moisture conditions can be controlled by the quantity and type of hydrophilic polymer coating on the particle surfaces.

Low molecular weight hydrophilic polymers will release the particle matrix compound at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release particle matrix compound at a relatively fast rate. Polyethylene oxide (M.W. of 4,000,000) or partially hydrolyzed polyvinyl acetate will release at a relatively slow rate. Polyvinylpyrrolidone will release particle matrix compound at an immediate rate when in contact with underarm type of moisture.

In another embodiment a powder composition of the present invention includes a content of anti-caking ingredient, in a sufficient quantity to provide and maintain free-flow properties in the powder composition.

Suitable anti-caking agents include magnesium silicate, zinc silicate, calcium silicate, sodium aluminosilicate, silica aerogel, silica xerogel, bentonite, attapulgite clay, zinc stearate, magnesium palmitate, sodium phthalate, zinc sulfide, magnesium phosphate, zirconium oxychloride, and the like.

The present invention also contemplates the provision of a cosmetic powder such as a baby powder formulation. Illustrative of a novel baby powder product is a formulation which comprises a blend of (1) a hydrophilic polymer-coated bicarbonate crystallite ingredient as described hereinabove, and (2) between about 5–70 weight percent of cosmetic grade talc.

In a further embodiment this invention provides a powder composition which comprises a blend of (1) a hydrophilic polymer-coated bicarbonate crystallite ingredient, and (2) between about 0.05–10 weight percent of a biocidal ingredient, such as 2,4,4'-trichloro-2'-hydroxydiphenyl ether (Triclosan). A preferred biocidal ingredient is zinc oxide having an average particle size less than about one micron.

Other advantages are achieved by the practice of the present invention. As noted in the Background section of the specification, the relative densities of liquid and solid phases in a cosmetic stick or roll-on product directly affects the stability and esthetics of the formulations. Density matching of inorganic and organic phases is a significant factor in cosmetic stick and roll-on products. The present invention provides a hydrophilic polymer-coated bicarbonate deodorant ingredient of lower density which more closely matches the density of the organic matrix of a cosmetic stick or roll-on product than does uncoated bicarbonate ingredient.

When there is density matching of organic matrix and dispersed hydrophilic polymer-coated bicarbonate particle phases, a cosmetic stick or roll-on product has improved dimensional stability, and better esthetic appearance and "feel" when applied to human skin.

An antiperspirant-deodorant cosmetic stick or roll-on product in accordance with the present invention has exceptional properties for treating or preventing perspiration and malodor associated with human underarm perspiration. A present invention cosmetic stick or roll-on product can be applied effectively with safety and comfort for reduction of underarm perspiration and offensive odors.

The following Examples are further illustrative of the present invention. The components and specific ingredients are presented as being typical and various modifications can be derived in view of the foregoing disclosure within the scope of the invention.

EXAMPLE I

This Example illustrates a fluidized bed procedure for coating a particulate bicarbonate compound with a hydrophilic polymer in accordance with the present invention.

A fluidized bed vessel is utilized which is equipped with a Wurster air-suspension coater system (WARF) as described in U.S. Pat. No. 4,568,559 and U.S. Pat. No. 4,877,621.

A coating solution is prepared by dissolving polyethylene glycol (45 g, Poly-G 2000, Olin Corp.), and propylene glycol butyl ether (10 g, PPG 14, Americol) in ethanol (500 g)/water (75 g).

Sodium bicarbonate is utilized as the core matrix particles. The sodium bicarbonate (Particle Size Technology, Inc.) has an average particle size of about 5 microns, and 90 percent of the particles have a diameter less than 20 microns.

The sodium bicarbonate powder is charged into the coating chamber of the coater system.

Compressed air is introduced into the coating chamber, and the polymeric coating solution is sprayed on the air-suspended bicarbonate core matrix particles, until the coating weight is about 30% of the total dry weight of the coated particles.

The procedure is repeated, except that Hydroxypropylmethylcellulose (Methocel 60 HG, Dow Chemical Co.) is employed as the hydrophilic polymer.

The procedure is repeated, except that multodextrin (Lodex 10; Durkee Foods) or amylodextrin is employed as the water-soluble polymer, and 0.5 g of a surfactant is included in the solution (polyoxyethylenesorbitan monolaurate; Tween 20; ICI Americas, Inc.).

The coated particles consist of a hydrophilic polymer coating on an inner core of 2–10 crystallites of sodium bicarbonate. The coated particles have an average particle size of about 35 microns.

EXAMPLE II

This Example illustrates a procedure for the preparation of an antiperspirant-deodorant cosmetic stick product in accordance with the present invention.

A stainless steel tank is provided which is equipped with turbine agitation.

Silicone oil DC 245 (400 lbs, Dow Corning) and Dow DC 200 (37.50 lbs, Dow Corning) are charged to the mixing tank. Agitation (55–65 RPM) is initiated, and heating the liquid medium to 176° F. is commenced.

During the heating period, the following ingredients are added to the stirred liquid medium:

|  | lbs. |
| --- | --- |
| Lanette 18 DEO[1] | 175.00 |
| Castorwax MP-80[2] | 31.25 |
| ICI G-2162[3] | 6.25 |

[1] Stearyl alcohol; Henkel.
[2] Hydrogenated castor oil; RTD.
[3] PEG 25 PG stearate; ICI.

The mixture is stirred at 176° F. for about 30 minutes until the ingredients are melted and the liquid medium is homogeneous. The stirring speed is reduced to about 35 RPM, then Cyprus Supra A Talc 1625 (18.75 lbs, Cyprus) and Reach AZP 908 aluminum-zirconium tetrachlorohydrex glycine (312.50 lbs, Reheis) are added. The temperature is maintained at 176° F. for about 40 minutes until the fluid medium is uniform, and then the temperature is lowered to 154° F.

Polymer-coated sodium bicarbonate (140 lbs.) and Sobica F41 fragrance (6.25 lbs, Takasago) respectively are added with stirring to Silicone oil DC 245 (200 lbs, Dow Corning) in a second mixing tank at a temperature of 154° F. to form a homogeneous suspension medium. The sodium bicarbonate particles are pre-coated with amylodextrin as described in Example I.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 7 (ASTM Method D5).

EXAMPLE III

This Example illustrates a precipitation procedure for forming microcrystallites of potassium bicarbonate, and coating the microcrystallites with a hydrophilic polymer in accordance with the present invention.

A coating solution is prepared by dissolving polyethylene glycol (10 g, Poly-G 2000, Olin Corp.), propylene glycol butyl ether (5 g, PPG 14, Americol), and polyoxyethylenesorbitan monolaurate (1.0 g; Tween 20; ICI Americas, Inc.) in 1-propanol (300 g).

A solution of potassium bicarbonate (30 g) in water (100 g) is prepared The potassium bicarbonate solution is added dropwise to the coating solution with high speed stirring.

The admixture which forms is a suspension of potassium bicarbonate microcrystallites in the liquid medium. The liquid medium is concentrated to dryness by removal of water/1-propanol azeotrope under vacuum at 60° C. in a rotating evaporator.

The resultant dry powder is composed of particles which consist of a 33% by weight coating on an inner core of 2–10 microcrystallites of potassium bicarbonate. The microcrystallites have a particle size distribution substantially in the range of 0.1–5 microns.

In another embodiment, the potassium bicarbonate suspension admixture is concentrated until all of the water is removed azeotropically. The remaining liquid concentrate is utilized as a deodorant ingredient in a cosmetic stick or roll-on formulation. The blending of the liquid concentrate with the other formulation ingredients disperses the deodorant ingredient in the form of hydrophilic polymer-coated potassium bicarbonate particles, which are similar to the encapsulated bicarbonate crystallites described in Example I.

EXAMPLE IV

This Example illustrates the preparation of an antiperspirant-deodorant roll-on product in accordance with the present invention.

A roll-on formulation is prepared by blending the following proportions of ingredients:

|  | lbs. |
| --- | --- |
| Silicone oil DC 245 | 60.90 |
| Quaternium-18 hectorite clay (Rheox) | 10.00 |
| Reach AZP 908 | 23.00 |
| Encapsulated potassium bicarbonate[1] | 5.00 |
| Cab-o-Sil fumed silica (Cabot) | 0.60 |
| Sobica F41 | 0.50 |

[1] Prepared by an Example III type of precipitation procedure.

(1) Prepared by an Example III type of precipitation procedure.

The roll-on formulation exhibits excellent dimensional stability when packaged and maintained under storage conditions for six months.

What is claimed is:

1. A powder composition which is composed of particles having an average particle size between about 5–60 microns, and an average dimensional axial ratio between about 1–2.5 to 1, and wherein the particles comprise a hydrophilic polymer surface coating having an encapsulated core matrix content of at least two crystallites of water-soluble inorganic compound selected from alkali metal bicarbonate and ammonium bicarbonate; wherein the encapsulated bicarbonate crystallites in the core matrix have an average particle size between about 0.5–30 microns.

2. A powder composition in accordance with claim 1 wherein the encapsulated bicarbonate crystallites have a particle size distribution in which at least 80 percent of the particles have a particle size in the range between about 0.1–5 microns.

3. A powder composition in accordance with claim 1 wherein the encapsulated bicarbonate crystallites are sodium, potassium or ammonium bicarbonate or mixtures thereof.

4. A powder composition in accordance with claim 1 wherein the hydrophilic polymer coating of the particles comprises between about 5–50 weight percent of the dry particle weight.

5. A powder composition in accordance with claim 1 wherein the hydrophilic polymer coating of the particles is a polysaccharide derivative.

6. A powder composition in accordance with claim 1 wherein the hydrophilic polymer coating of the particles is a hydrocolloid.

7. A powder composition in accordance with claim 1 wherein the hydrophilic polymer coating of the particles is a starch derivative.

8. A powder composition in accordance with claim 1 wherein the hydrophilic polymer coating of the particles is multodextrin or amylodextrin or a mixture thereof.

9. A powder composition in accordance with claim 1 wherein the hydrophilic polymer coating has a content of between about 0.5–40 weight percent of a water-insoluble polymer, based on the coating weight.

10. A powder composition in accordance with claim 1 which has a content between about 1–20 weight percent of particulate anti-caking ingredient and is free-flowing.

11. A powder composition in accordance with claim 1 which has a content between about 5–70 weight percent of talc, and the composition is a cosmetic powder formulation.

12. A powder composition in accordance with claim 1 which has a content between about 0.05–10 weight percent of biocidal ingredient.

13. A powder composition in accordance with claim 12 wherein the biocidal ingredient is zinc oxide having an average particle size less than about one micron.

* * * * *